(12) United States Patent
Feingold

(10) Patent No.: US 9,010,817 B2
(45) Date of Patent: Apr. 21, 2015

(54) LENS HOLDER APPARATUS AND SYSTEM AND METHOD

(71) Applicant: Vladimir Feingold, Laguna Niguel, CA (US)

(72) Inventor: Vladimir Feingold, Laguna Niguel, CA (US)

(73) Assignee: Presbibio, LLC, Irvine, CA (US)

( * ) Notice: Subject to any disclaimer, the term of this patent is extended or adjusted under 35 U.S.C. 154(b) by 0 days.

(21) Appl. No.: 13/784,725

(22) Filed: Mar. 4, 2013

(65) Prior Publication Data

US 2013/0240396 A1    Sep. 19, 2013

Related U.S. Application Data

(63) Continuation-in-part of application No. 12/705,523, filed on Feb. 12, 2010, now Pat. No. 8,869,975.

(51) Int. Cl.
| | |
|---|---|
| *A61F 9/007* | (2006.01) |
| *B25B 9/02* | (2006.01) |
| *B65D 6/00* | (2006.01) |
| *B65B 5/00* | (2006.01) |
| *A61F 2/16* | (2006.01) |
| *B65D 51/26* | (2006.01) |
| *A61F 2/00* | (2006.01) |

(52) U.S. Cl.
CPC . *B65D 11/00* (2013.01); *B65B 5/00* (2013.01); *A61F 2/1691* (2013.01); *B65D 51/26* (2013.01); *A61F 2/0095* (2013.01); *A61F 2/1662* (2013.01)

(58) Field of Classification Search
USPC .......... 294/1.2, 99.2; 623/6.11, 6.12; 206/5.1; 606/107

See application file for complete search history.

(56) References Cited

U.S. PATENT DOCUMENTS

| | | | | |
|---|---|---|---|---|
| 5,100,410 | A | * | 3/1992 | Dulebohn ...................... 606/107 |
| 5,176,701 | A | * | 1/1993 | Dusek et al. .................. 606/207 |
| 5,217,464 | A | * | 6/1993 | McDonald .................... 606/107 |
| 6,360,883 | B1 | * | 3/2002 | Haq et al. ...................... 206/205 |
| 6,605,093 | B1 | * | 8/2003 | Blake ............................. 606/107 |
| 8,454,687 | B2 | * | 6/2013 | Feingold ...................... 623/6.12 |
| 2007/0055370 | A1 | * | 3/2007 | Sorochkin et al. ........... 623/6.12 |
| 2008/0243138 | A1 | * | 10/2008 | Dishler et al. ................ 606/107 |
| 2008/0275462 | A1 | * | 11/2008 | Feingold et al. ............. 606/107 |
| 2009/0057167 | A1 | * | 3/2009 | Rathert ......................... 206/205 |

* cited by examiner

*Primary Examiner* — Dean Kramer
(74) *Attorney, Agent, or Firm* — Lawrence S. Cohen

(57) ABSTRACT

An apparatus for safely retaining an eye implant lens for transport and access for inspection and use in which a holding apparatus has a chamber for holding a lens. In one embodiment the chamber has a pin on which a lens can be placed and a ramp leading to the pin so that a gripping member can slide up the ramp into proper placement to grip the lens and remove it. The gripper can be configured so that after removing the lens from the holding apparatus, it can be used to implant the lens. Also, a system including the apparatus and a bottle assembly that will hold the apparatus in the bottle. A method for holding an eye implant lens in which a lens is placed in the apparatus which can then be placed in a bottle assembly.

4 Claims, 20 Drawing Sheets

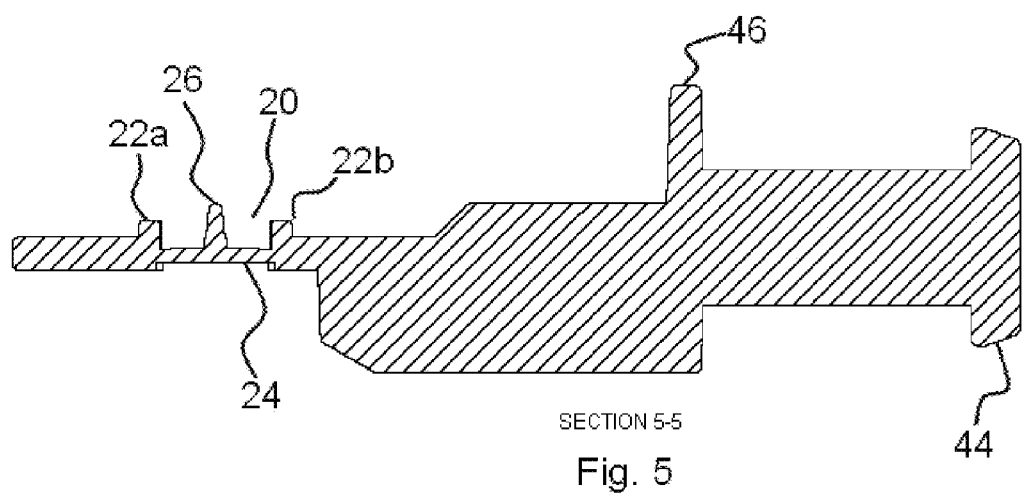
Fig. 5
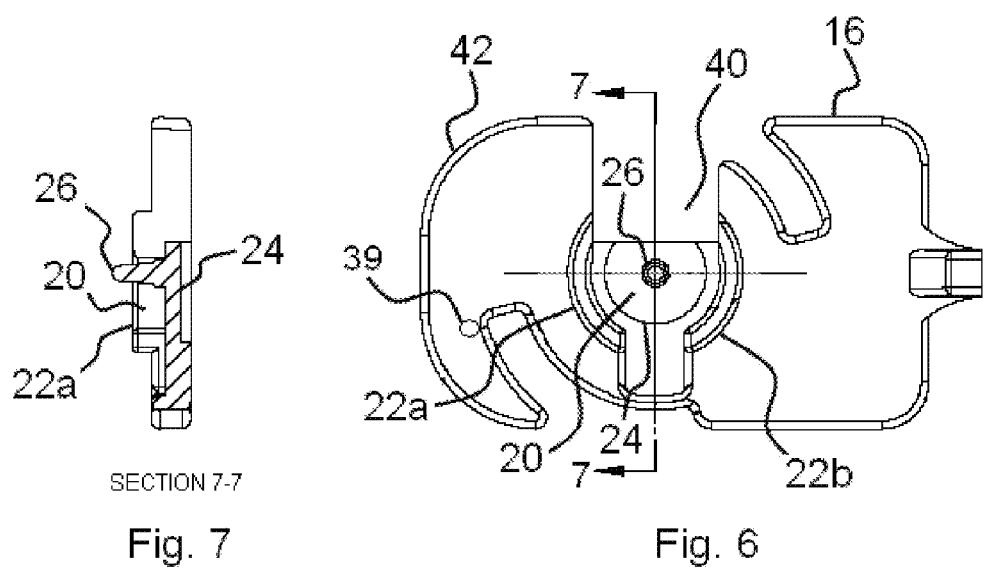
Fig. 7
Fig. 6

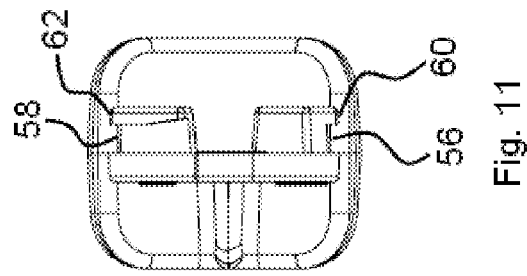
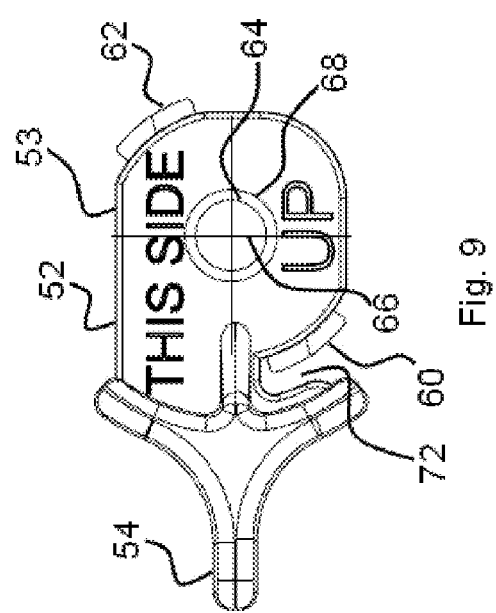
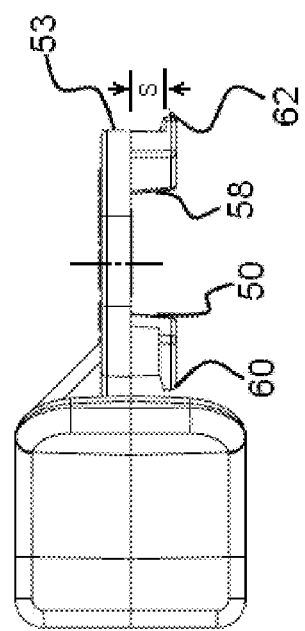

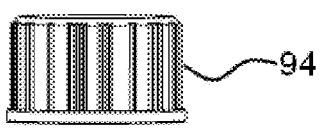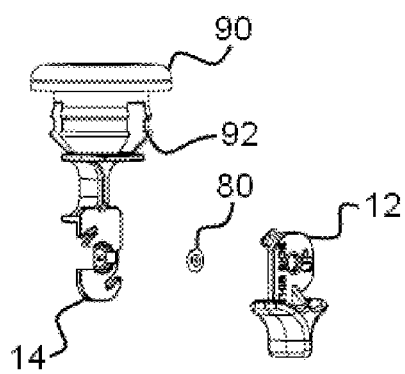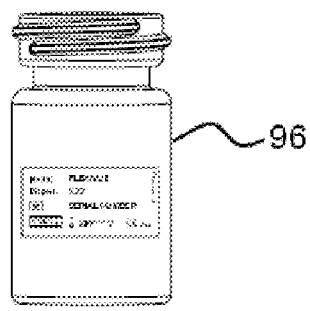
Fig. 18
Fig. 19

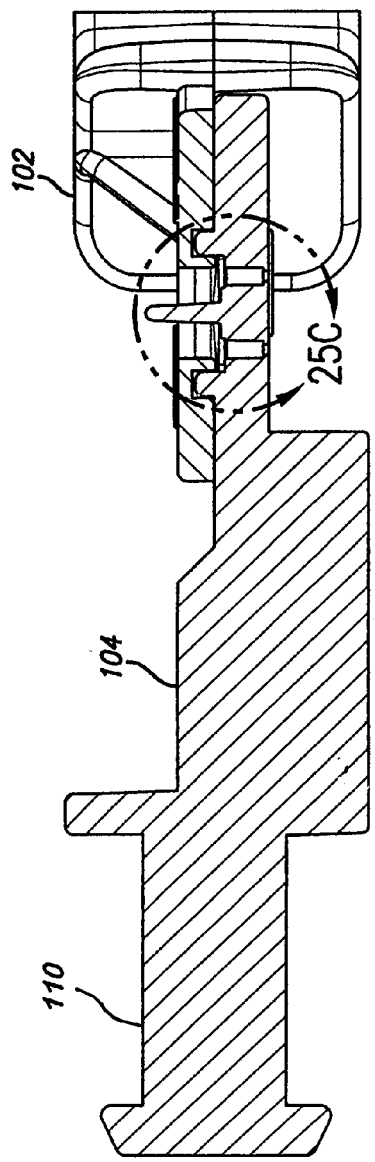
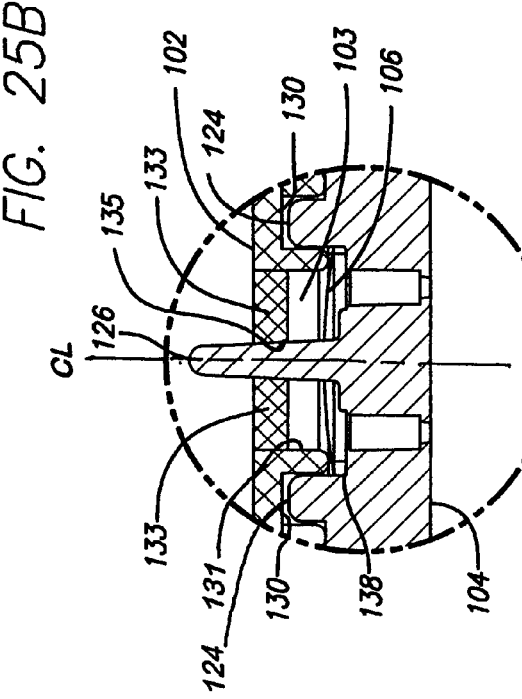
FIG. 25B
FIG. 25C

LENS HOLDER APPARATUS AND SYSTEM AND METHOD

This application is a continuation-in-part of application Ser. No. 12/705,523 filed on Feb. 12, 2010 the content of which is incorporated herein by reference and the priority of which is claimed.

BACKGROUND

1. Field of the Invention

The invention relates to holding and transport devices for holding lenses during transport and storage such as from the point of manufacture to the point of usage and to facilitate inspection and access.

2. General Background

In the field of eye surgery, there are two types of eye lens implants, intracorneal and intraocular implants. In each of these a small lens is implanted into the eye in the cornea or in or adjacent the iris. The lenses are very small such as in the case of intracorneal lenses in the range from 1 mm to 4 mm in diameter and in the case of intraocular lenses in the range from 4 mm to 8 mm in diameter. From the point of manufacture to implantation the lens has to be carefully maintained in some kind of container. During the operations from manufacture, shipment and storage to implantation, handling of the lens can be detrimental and risky to the lens itself and is inconvenient for handling such small items. There is a need to reduce any transfer of the lens from one environment to another and to allow access to the lens for testing and for use with the minimum of actual handling of the lens.

BRIEF DESCRIPTION OF THE DRAWINGS

For a further understanding of the objects and advantages of the present invention, reference should be had to the following detailed description, taken in conjunction with the accompanying drawings, in which like parts are given like reference numbers and wherein:

FIG. 5 is a section view through 5-5 of FIG. 3.

FIG. 6 is an enlarged view of the circled portion A of the lower case in FIG. 3.

FIG. 7 is a section view through 7-7 of FIG. 6.

FIG. 9 is a top view of the upper case.

FIG. 10 is a front view of the upper case.

FIG. 11 is a side view of the upper case.

FIG. 18 is an exploded view of the lens holder apparatus, a lens held in it, the retaining plug and the bottle.

FIG. 19 is a view of the lens holder apparatus inside a bottle.

FIG. 25B is the section view D-D.

FIG. 25C is an enlarged detail view of a portion of FIG. 25B.

DETAILED DESCRIPTION

The invention is in the field of transporting eye implant lenses and the ability to conveniently test and access such lenses. Embodiments include a lens holder apparatus and a system that combines a lens holder apparatus with a container. One feature is that a lens is trapped in a lens holder apparatus for minimum movement. Another feature is to be able to inspect the lens while it is in the lens holder apparatus and also while it is in the container. The invention provides several functions that are important in the transportation, storage and testing of such lenses. The functions include protecting the lens, allowing testing of the lens while it remains retained in the lens holder apparatus and allowing for convenient placement of the lens into the lens holder apparatus and for convenient removal of the lens at the time it is to be used. Embodiments of the lens holder apparatus include two parts that define a chamber into which a lens can be placed, the two parts being separable and joinable to allow a lens to be installed and later removed. Transparent portions of the two parts are aligned so as to allow optical testing and observation of the lens. The lens holder apparatus also has a handle which can be fitted to a part in a bottle assembly so that it will stay in a fixed position in the bottle.

The invention will be further understood from the following description in conjunction with the drawings.

Figure 1:
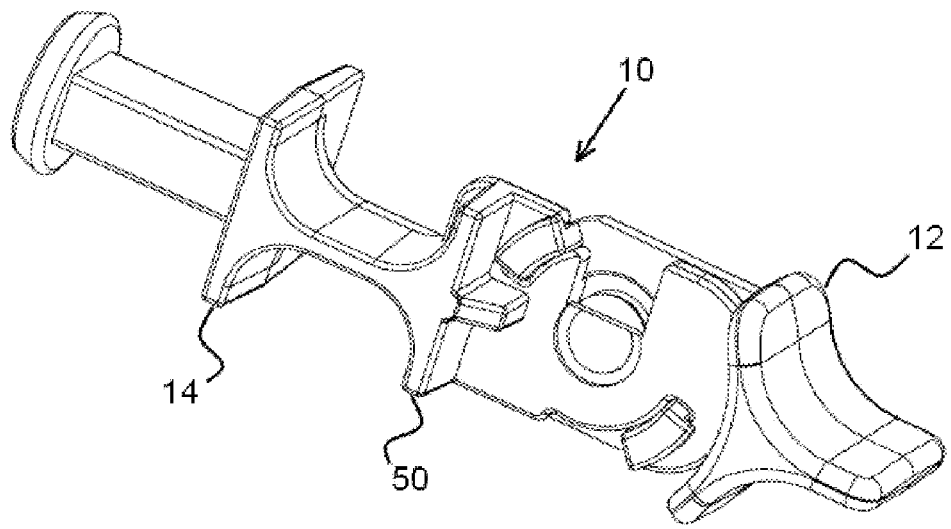
FIG. 1 is a perspective view of the assembled lens transport apparatus.
Figure 2:
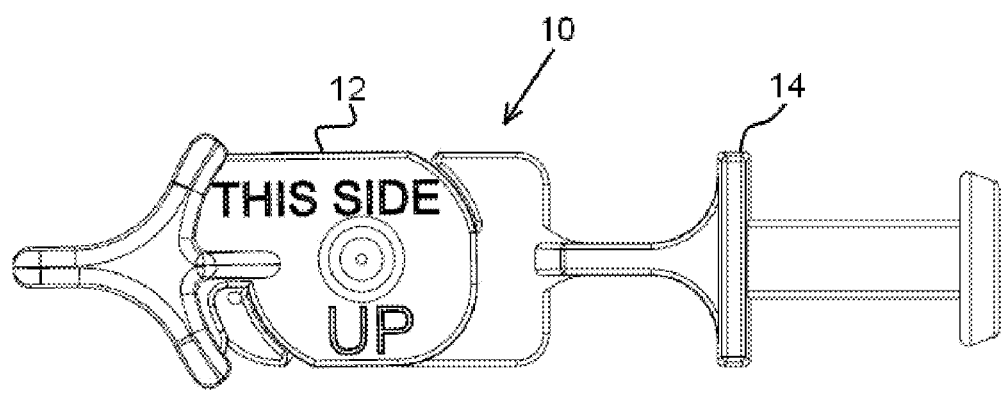
FIG. 2 is a top view of the assembled lens transport apparatus.
Figure 3:
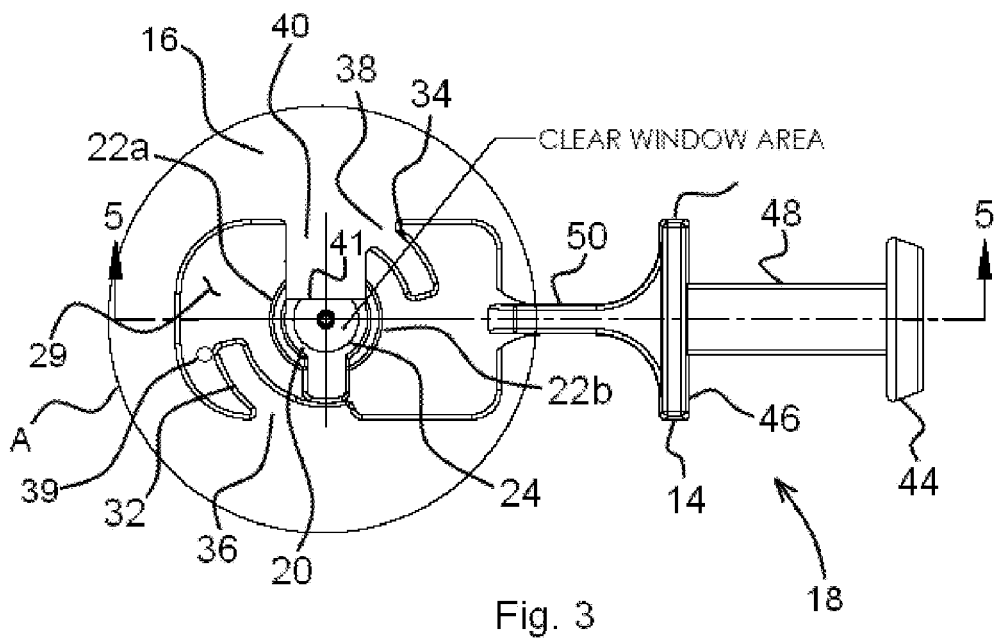
FIG. 3 is a top view of the lower case.
Figure 4:
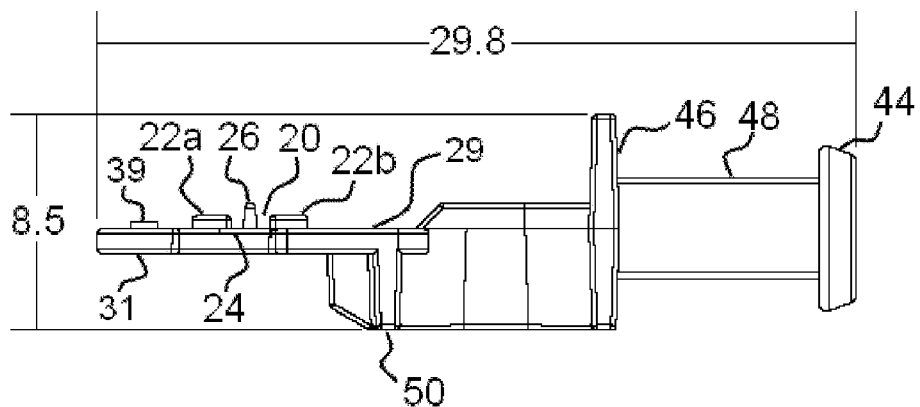
FIG. 4 is a side view of the lower case.
Figure 8:
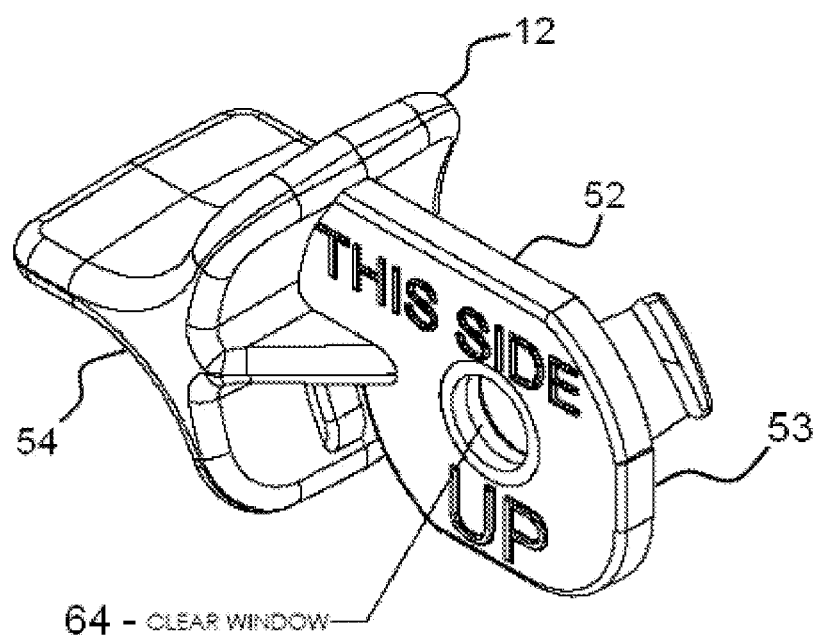
FIG. 8 is a perspective view of the upper case.

FIGS. 1 and 2 show a perspective view and a top view of the lens holder apparatus 10 in its assembled configuration for holding a lens. It has two parts, an upper case 12 and a lower case 14. In FIGS. 1 and 2 the lens holder apparatus 10 is in its fully assembled form, that is the upper case 12 and the lower case 14 are in the final position for holding a lens. In this description the term "lens" refers to all types of eye lens implants.

FIGS. 3 through 7 illustrate an embodiment of the lower case 14. The lower case 14 has a generally flat containment portion 16 (shown within the circle A in FIG. 3) and a handle portion 18. With additional reference to FIGS. 16 and 17, the containment portion 16 has a lower case space element 20 which is defined by circular partial bosses 22a and 22b. Within space portion 20 is a clear window area 24 and in its center is a post 26 which has a shoulder 28 above the window area 24. An axis 30 is defined by the center of the window area, and extending through the post 26. The window area is an integral part of the containment portion 16 and is made transparent during the molding process to make the lower case 14 in a manner known in the plastic molding art.

The containment portion 16 of the lower case 14 has an inner surface 29 and an outer surface 31 defining a thickness T. It has slots 32 and 34 that extend in a circular shape around the axis 30 and they are generally oppositely located. Each slot has an opening 36 and 38 respectively. A latch is defined by a protrusion 39, in this embodiment circular, upward from the inner surface 29. The containment portion 16 has an opening 40 extending from one side toward the axis and ending at edge 41 just into the window area 24, the opening 40 serving to facilitate removal of a lens as will be explained below. The handle portion 18 has a retainer knob 44 and a tang 46, a spacer bar 48 and support beams 50 to which the containment portion 16 is mounted.

The lower case 14 is molded from a single piece of plastic, a polysulfone; Solvay Advanced Polymers UDEL-P1700 CL2611 and UDEL P1700 NT 06 being exemplary. The clear window area 24 is made by polishing on each side. The polished surface is achieved by inserting pins with a highly polished surface in the mold.

The upper case 12 is shown in FIGS. 8-11 and FIGS. 16 and 17. It has a containment portion 52 and a handle 54. The containment portion 52 is built up from a generally flat body 53. From a lower side of the body 53 tabs 56 and 58 project. The tabs have rims 60 and 62 respectively. The rims 60 and 62 have a wedge shape commencing thinner at a front and thicker toward the rear. This wedge shape has the effect of a gradual reducing of the space S between the rim and the surface of the body 53. As will be seen, the thickness T of the containment portion 16 of the lower case 14 will be gripped in the space S so that the wedge shape accommodates the assembly to result in a secure assembly. A clear circular window area 64 defines a center at 66 in a space element 68 bounded by a circular rim 70 that defines the upper case space portion. The tabs 56 and 58 are circular around the center 66. The axis 30 runs through the center 66. The window 64 has a central aperture into which the post 26 extends when the upper and lower case are assembled. The upper case has a slot 72.

The window areas 24 and 64 (also called transparent portions) can be made integral with their respective case portions or can be made separately and installed. They are configured to allow optical testing of the lens inside the chamber.

Figure 12:
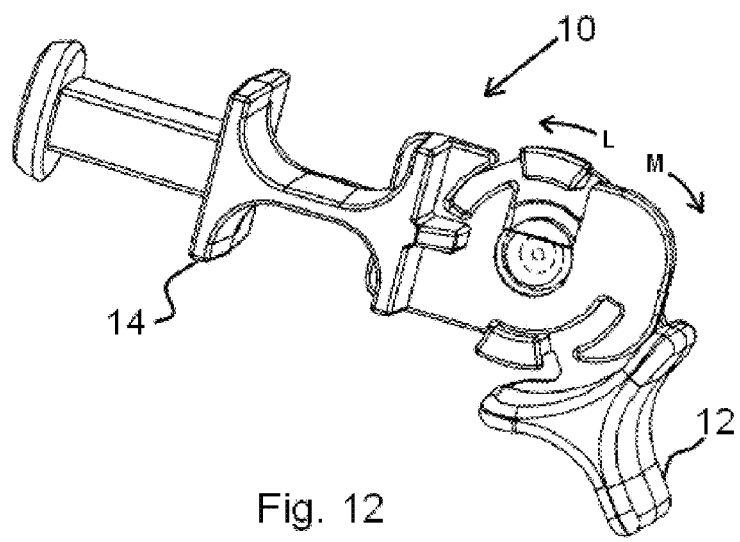
FIG. 12 is a bottom perspective view of the upper case and the lower case in the position ready for assembly.
Figure 13:
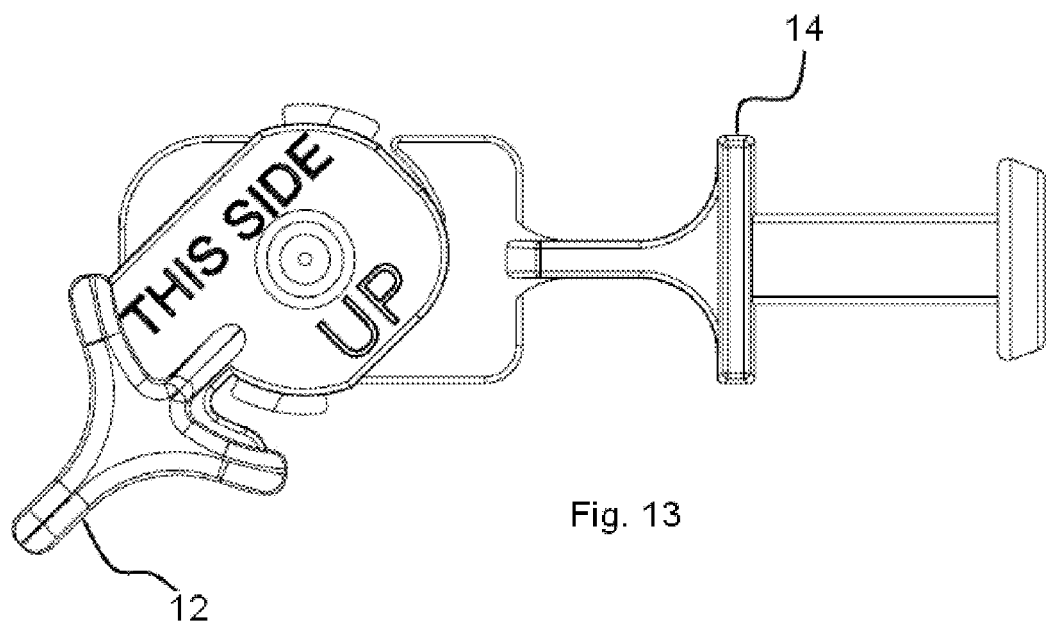
FIG. 13 is a top view of the upper case and the lower case in the position ready for assembly.
Figure 15:
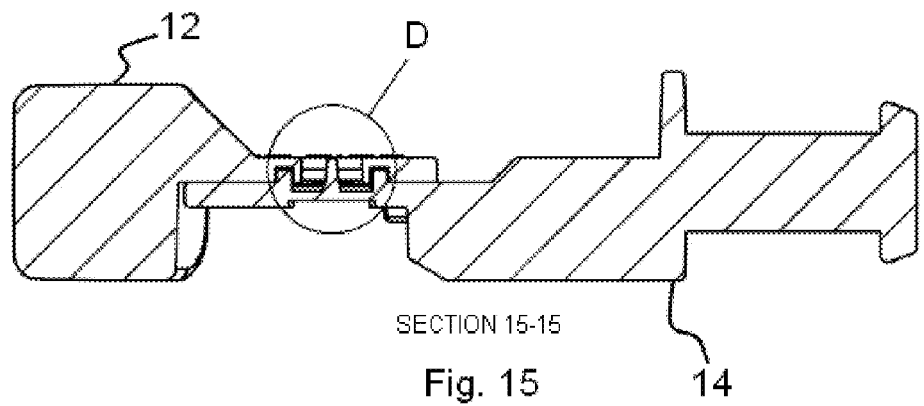
FIG. 15. is a sectional view through 15-15 of FIG. 15.

To employ the lens holder apparatus, the upper case and the lower case are connected after a lens 80 has been fitted on the post 26. The procedure for connecting them is shown in FIGS. 12 and 13. FIG. 12 is looking up from under the lower case 14. The upper case 12 is in position with the tabs 56 and 58 of the upper case adjacent the openings 36 and 38 of the slots 32 and 34 of the lower case. FIG. 13 is looking down from over the apparatus with the upper and lower cases in the same ready positions as in FIG. 12.

Figure 14:
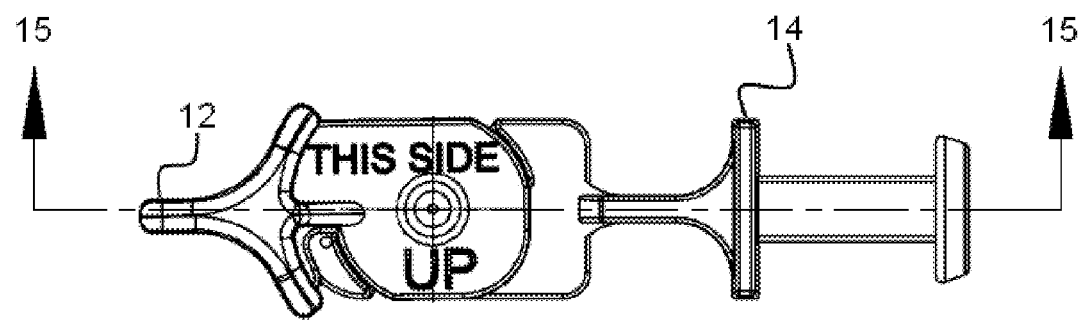
FIG. 14 is a top view of the apparatus with the upper case and the lower case in the assembled position.

To make the assembly the upper and lower cases 12 and 14 are rotated relative to each other as exemplified by arrows L and M in FIG. 12 into the final assembled position as shown in FIG. 14. Note the designation "THIS SIDE UP" on the top of upper case 12, which is an instruction to hold the parts so that the lens does not fall out before they are connected, and later for inspection and removal. In the step of rotating the upper and lower cases the tabs 56 and 58 enter the slots 32 and 34 while the rims 60 and 62 grip the containment portion 16. Also, at the end of the rotation step the latch 39 pops (a "click" can be heard) into the slot 72 to provide a positive assembled condition.

Figure 16:
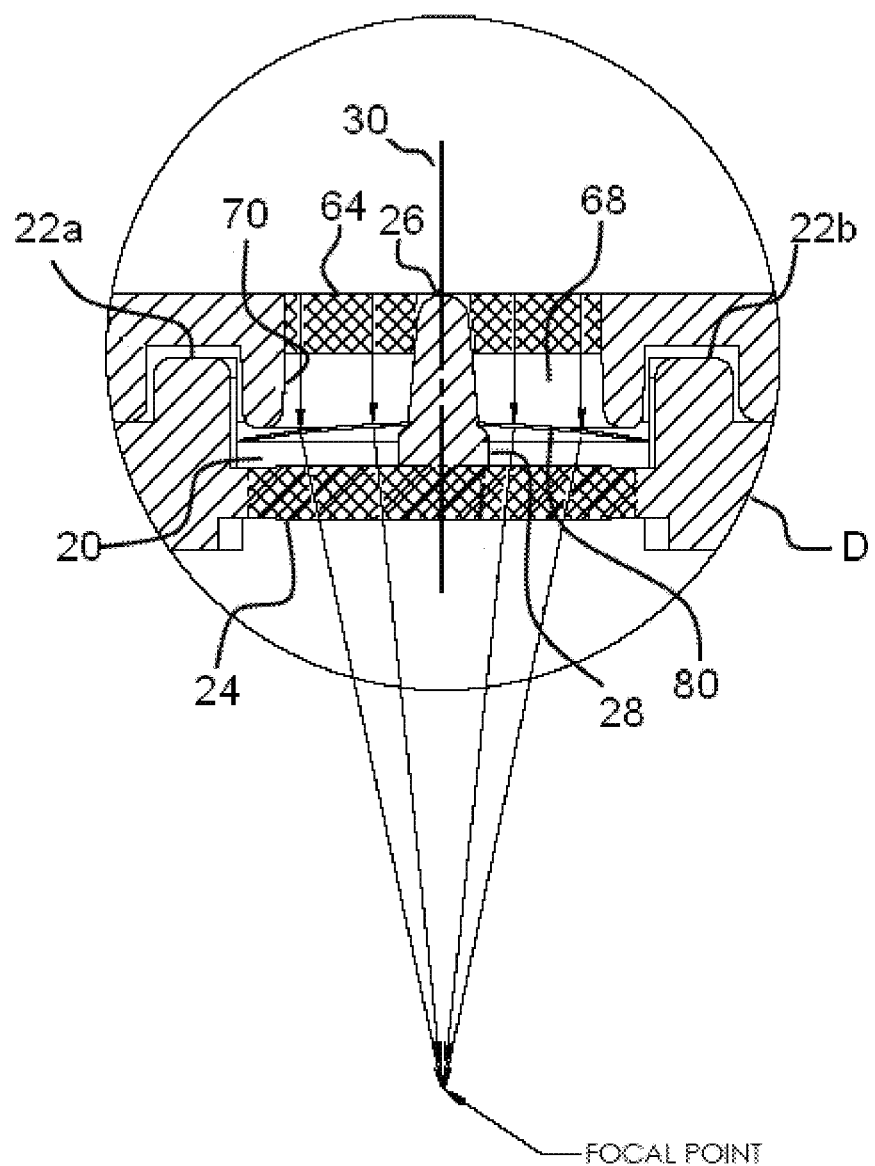
FIG. 16 is an enlarged detail sectional view of portion B of FIG. 15 showing the storage chamber with a lens.

FIG. 16 shows an enlarged sectional view D of the upper case and the lower case when assembled with a lens 80 in the storage space which is defined by the space element 20 of the lower case and the space element 68 of the upper case. A lens 80 is in place on the post 26 seated on the shoulder 28.

Figure 17:
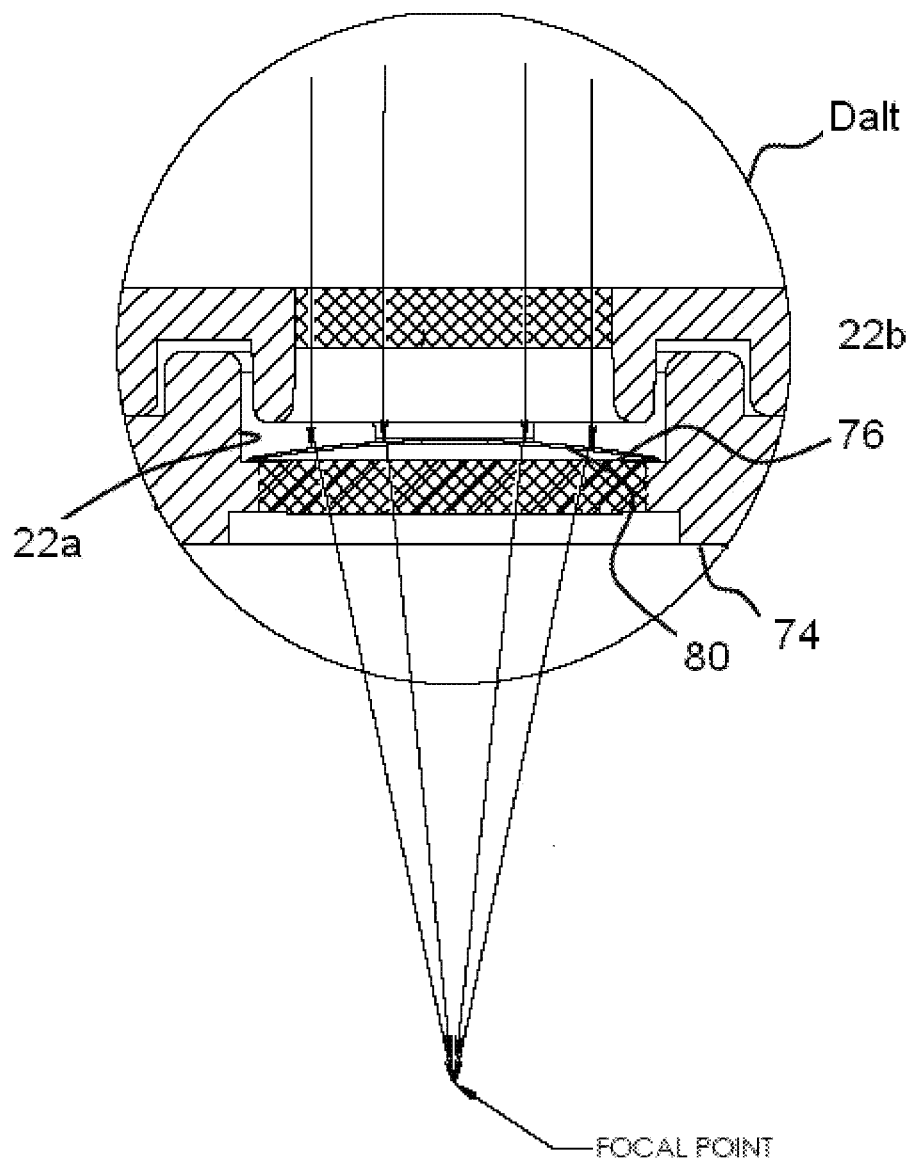
FIG. 17 is an enlarged detail sectional view of an alternative storage chamber with a lens.

An alternative embodiment is shown in FIG. 17. In this embodiment, the structure of the lower case 74 does not have a post to support the lens, instead the lens rests on the floor 76 of the lower case 74, inside the bosses 22a and 22b. Also, in this embodiment the window 64 of the upper case 12 does not have a hole. The difference in this embodiment is that the lens is not positively held, although it is sufficiently secure, as compared to the structure of FIG. 16 in which the lens is secured on the post.

When access to the lens 80 is desired, as for implanting it, a gripping device such as surgical forceps or lens insertion devices can be moved into the recess 40, with one arm above and one arm below the lens, to grip it between the arms. Thus the recess allows the arms of a gripping device access to the lens 80.

With the construction of the lens transport apparatus as described above, it can be carried in a custom made or a commercially available container. FIG. 18 shows the lens holder apparatus 10 held in a flexible plastic plug 90 by the handle portion 44 being pushed into the grip 92 of the plug 90. Then the plug 90 is installed in a bottle 96 and the cap 94 screwed on. It would also be possible to provide a container 96 as in FIG. 19 having flat sides which would allow inspection through the flat sides without the need to remove the lens holder apparatus from the container. In use the bottle would typically be filled with saline solution or balanced salt solution.

The inspection of the lens can be done using a common lensometer. The lens holder may be inserted in a glass cuvette filled with liquid. Such inspection methods are common for contact lenses measurement of diopter power and resolution.

Lens inspection with the invention is, for example, for optical (diopter) power, size of the lens, and cosmetics such as surface quality. In FIGS. 16 and 17 light rays are illustrated to show how measurements can be made.

After the lens transport apparatus has arrived at the point where the lens is to be implanted, the lens is removed with a device specially designed to grip it. In some cases that device will be used just to take lens out, but in most cases that device will also be the insertion device for inserting the lens into the eye. It is at this point that the recess 40 comes into use because the recess 40 allows a gripping device to be centered and access to both the top and bottom of the lens to grip it and remove it.

Further embodiments are shown in FIGS. 20-27.

In these embodiments, in one aspect the upper and lower cases form a chamber for holding an eye implant lens in which the lower case has walls defining a well so that a liquid such as saline solution or balanced salt solution can be contained to form a bead whose surface tension keeps the lens in an unfolded state. The well has drainage holes which along with a lengthened pin keeps the lens from floating off the lens holder when it is open.

The case assembly may be contained in a vial as described below and when it is removed from the vial, the bead of saline or balanced salt solution is retained in the chamber around the lens, both under and above its surface.

In another aspect the lower case has a ramp sloping downwardly away from the pin. This allows a gripping device (also called an inserter) to be centered in referenced to the lens and placed on the ramp and readily moved up the ramp into the correct position to grip a lens which is on the pin. The gripping device has an upper fork arm and a lower fork arm. In use the lower fork arm is moved into contact with the ramp and is moved up the ramp into position under the lens, with the upper fork arm over the lens. Then the fork arms can be brought together to grip the lens and remove it.

In a further aspect there is a tab that extends circumferentially away from the pin, on the ramp to further guide the gripping device. The lower fork arm of the gripping device engages the tab between its forks which then guides the gripping device into correct position at the lens as it is moved up the ramp.

The pin, in these embodiments is higher than prior embodiments and extends from the lower case into a recess in the upper case. That way if the lens is lifted by the saline or balanced salt solution it will not lift off the pin. The recess in the upper case can have a transparent window so as to allow optical access for inspection.

For use with the embodiments of the case assembly a lens inserter device is provided. The lens inserter has at a working end two forked members an upper fork arm and a lower fork arm, which are spaced apart. Each of them has two forks which are laterally spaced-apart. In use, the working end is inserted so that the lower fork arm slides along the ramp into position, with its spaced apart forks passing on opposite sides of the pin. In that way, by the ramp raising it to be aligned with the lens and positioning the forks on either side of the pin, the lens on the pin is properly positioned between the upper and lower fork arms. Then, with the lower fork arm beneath the lens and the upper fork arm over the lens, the fork arms are brought together to grip the lens which is then lifted off the pin. The tab contributes additional guidance so that before the forked working end is constrained by the pin, as it is guided up the ramp, the tab is between the forks of the lower fork arm and aligns it with the pin.

Figure 20:
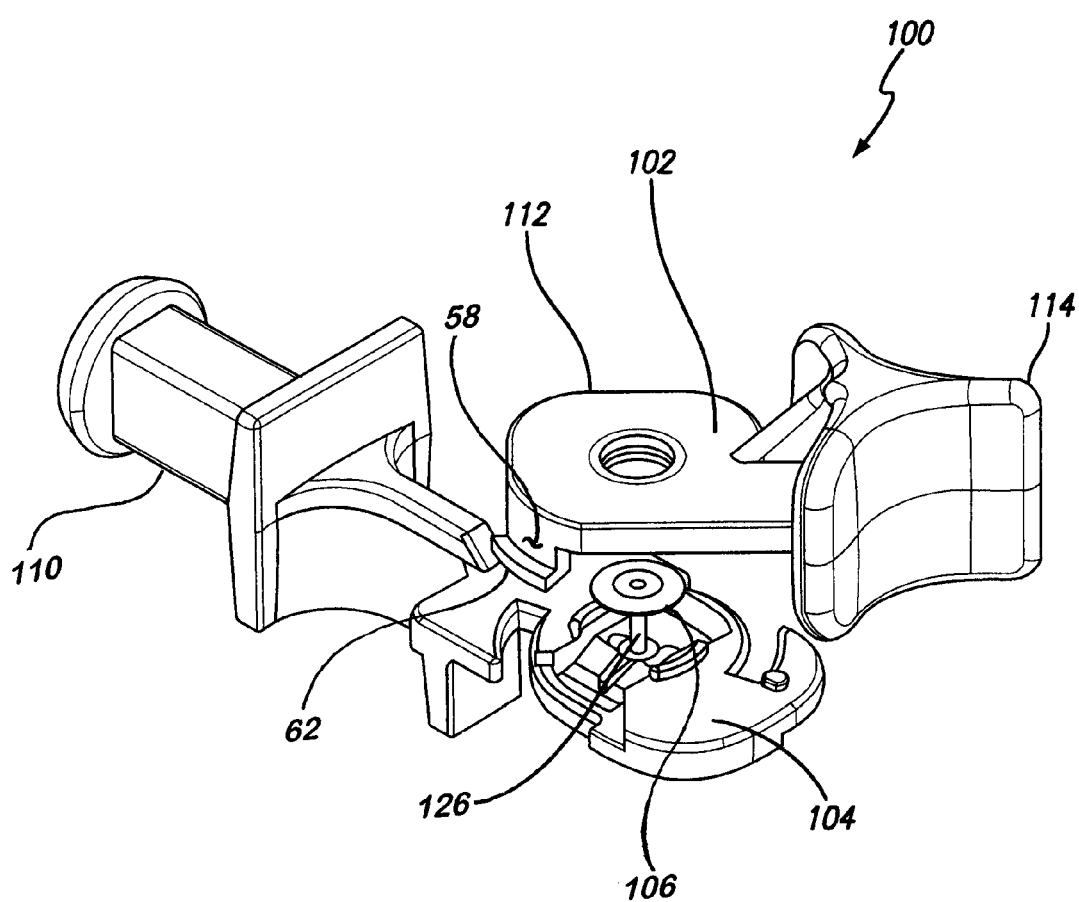
FIG. 20 is a perspective view of the lens holder apparatus with the upper case and the lower case ready for a connection and a lens in place.
Figure 21A:
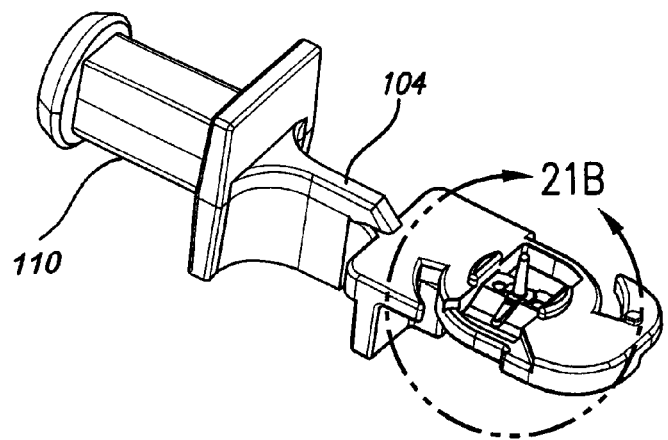
FIG. 21A is a perspective view of the lower case.
Figure 21B:
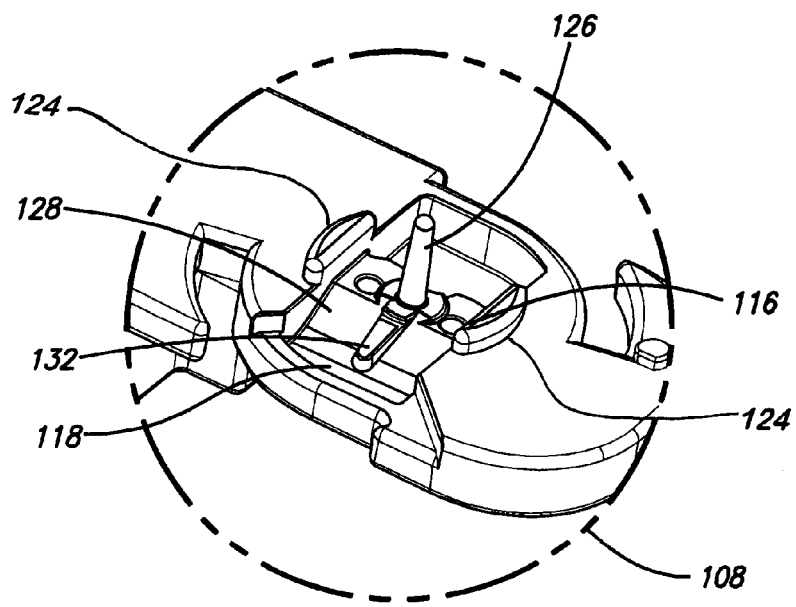
FIG. 21B is an enlarged partial view of the lower case of FIG. 21A.
Figure 22A:
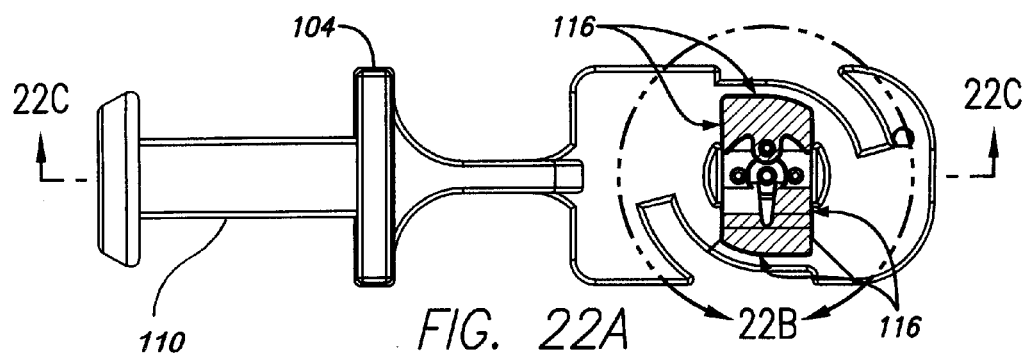
FIG. 22A is a top view of the lower case with an outline of the well.
Figure 22B:
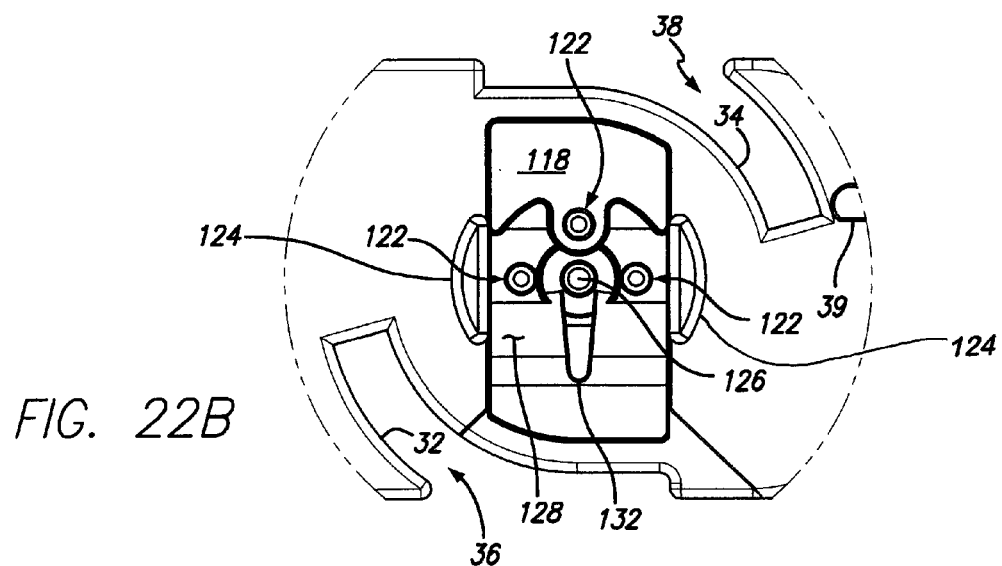
FIG. 22B is an enlarged partial view of the lower case of FIG. 22A.
Figure 22C:
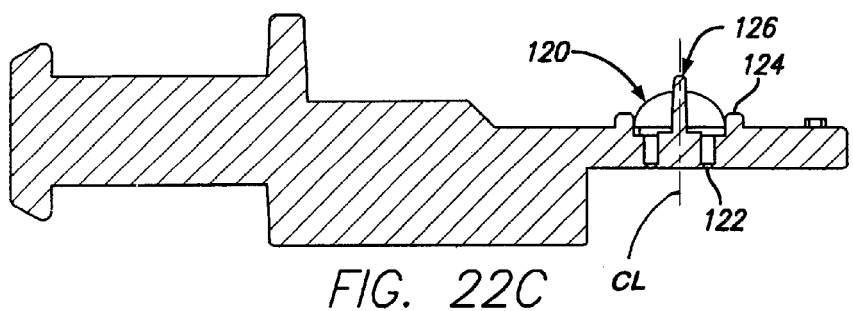
FIG. 22C is a section C-C through FIG. 22A.
Figure 23A:
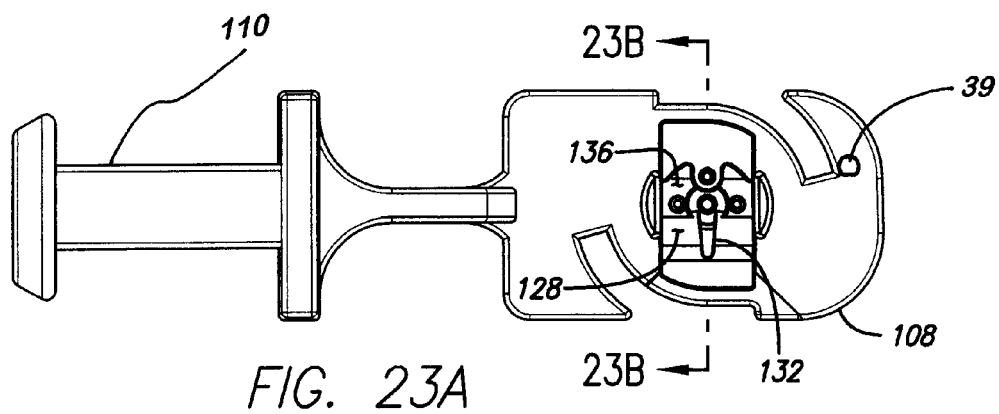
FIG. 23A is a top view of the lower case indicating a section F-F
Figure 23B:
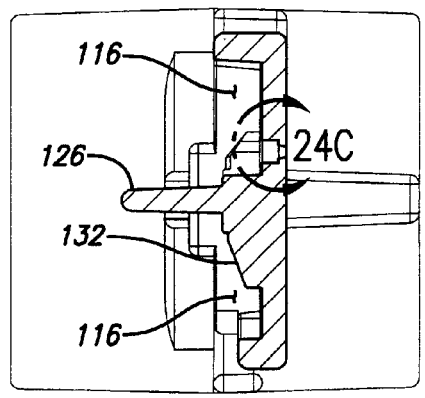
FIG. 23B is the section view F-F
Figure 24C:
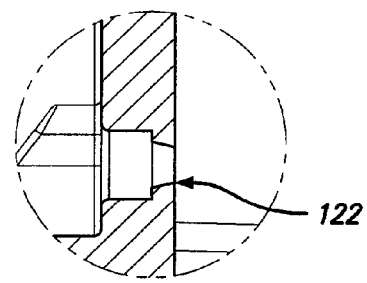
FIG. 24C is a sectional view of a portion of FIG. 24B
Figure 24A:
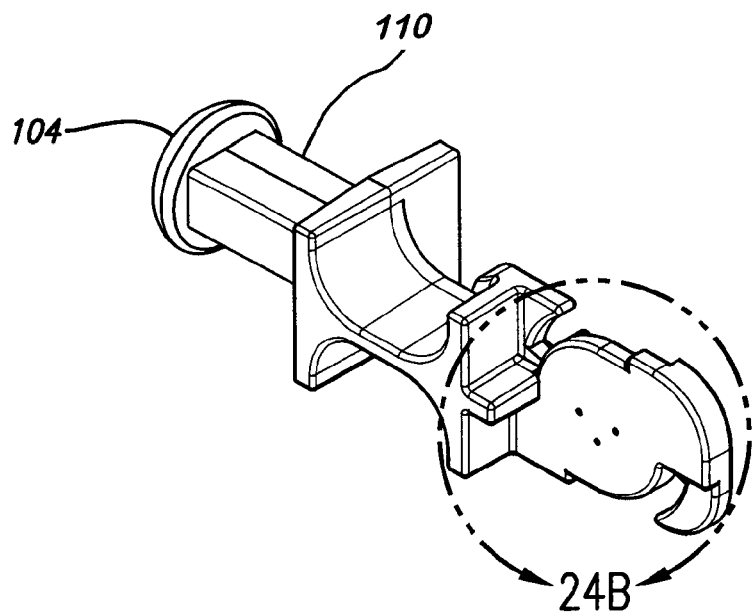
FIG. 24A is a perspective bottom view of the lower case
Figure 24B:
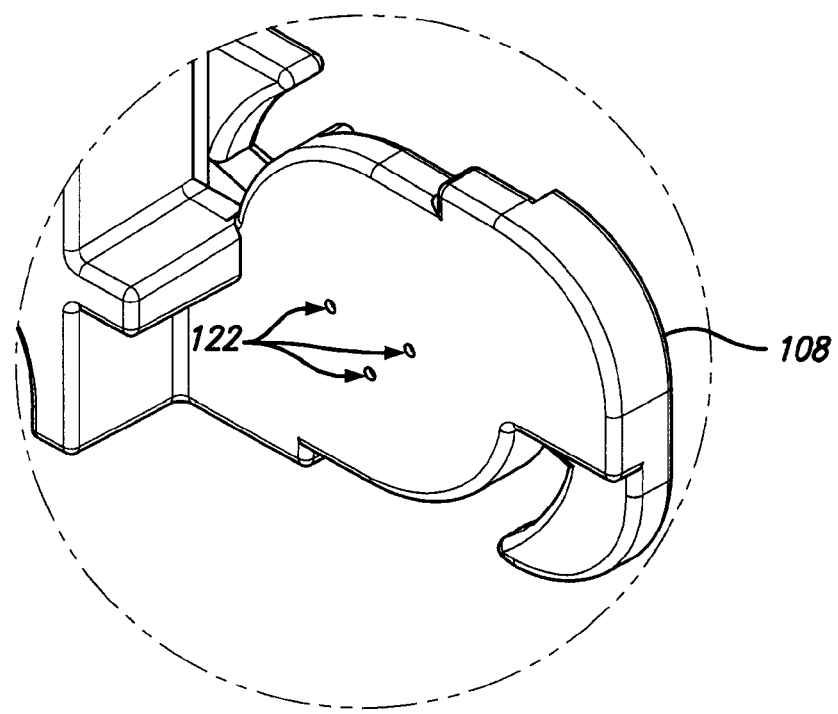
FIG. 24B is an enlarged detail view of a portion of FIG. 24A

Referring to FIGS. 20, 21A and 21B there is shown a lens holder 100 having an upper case 102 and a lower case 104 in relative position ready to be connected into the final position for holding a lens (as in FIG. 20). A lens 106 is shown properly positioned to descend onto pin 126. The lower case 104 has a containment portion 108 (shown within the circle 21B in FIG. 21A and in FIG. 21B) and a handle portion 110. The upper case 102 has a containment portion 112 and a handle 114. The structure for connecting and disconnecting the upper and lower cases is a described above.

FIGS. 21A, 21B and 22A-C, 23A-B, 24A-C are detailed views of the lower case 104 in which walls 116 (see FIGS. 22A and 23B) form a well 118 (shown in slanted lines) for the purpose of containing saline or balanced salt solution bead 120 or other liquid. Drainage holes 122 are optionally provided. Curbs 124 extend upwardly on either side of the well 118 and the pin 126 extends upwardly, its centerline CL (see FIGS. 22C and 25C) defining the center of rotation for connecting and disconnecting the upper and lower casings. In this embodiment, the pin 126 is higher than shown in FIG. 16 (see FIG. 25C) so as to ensure that the lens 106 will not be floated off it by the saline or balanced salt bead 120.

A ramp 128 commences from a lower level in the well 118 and extends upwardly toward the pin 126 which is at the top of the ramp 128. A tab 132 extends from the pin 126 diametrically along the ramp 128 at a height so as to provide a sufficient height as will be appreciated from description below.

Figure 25A:
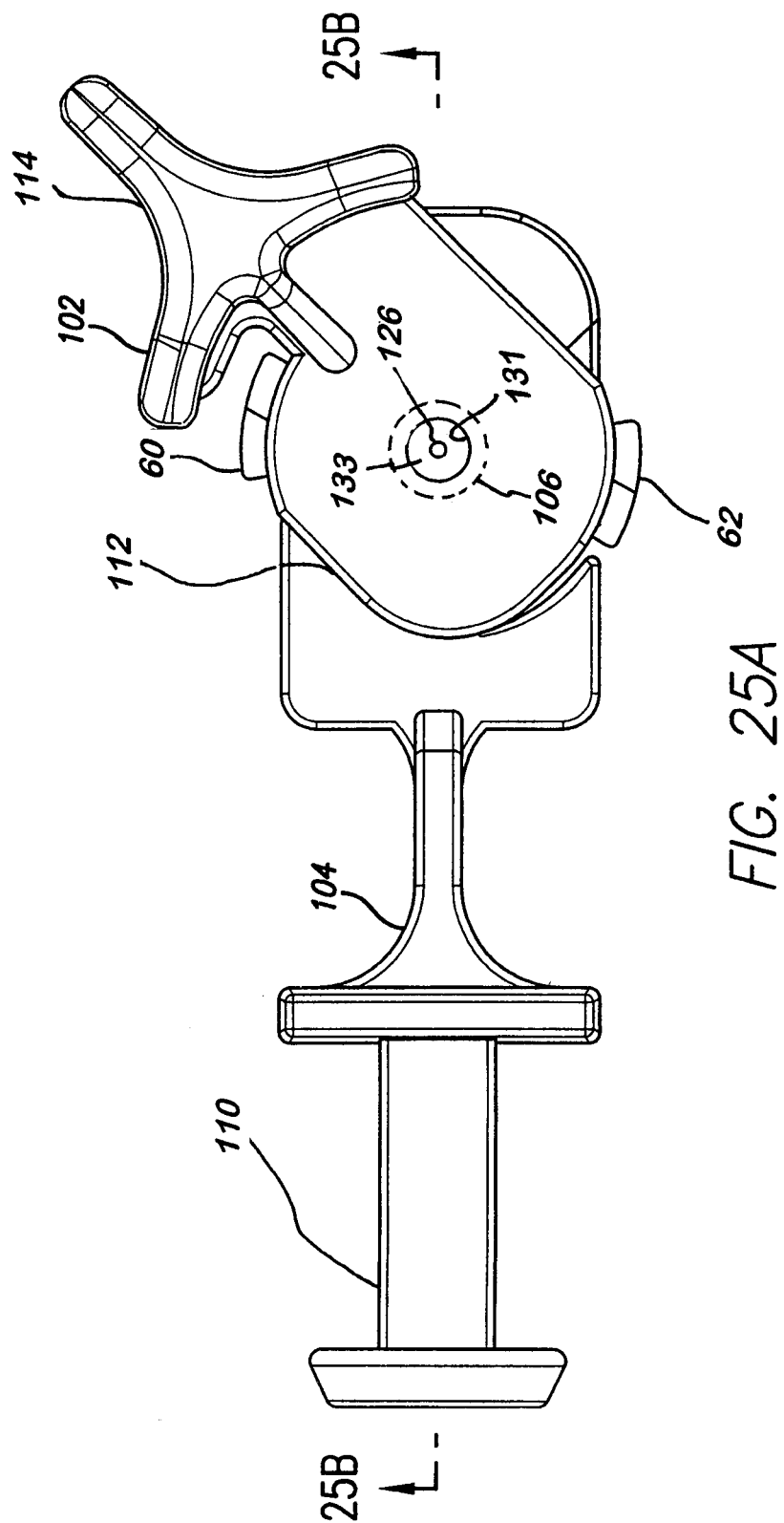
FIG. 25A is a top view of the upper and lower cases positioned for being connected and indicating a section D-D.

FIGS. 25A-C show the lens holder with the upper case 102 in position to connect with the lower case 104 upon rotation and with a lens 106 in place. Although not shown, saline or balanced salt could be in it. The upper case 102 has channels 130 that upon rotation for connecting will engage with curbs 124 (see FIG. 25C). Centerline CL shows that the rotation to connect and disconnect the upper and lower case elements is centered on the pin 126. The upper case 102 has a roof having an aperture 135 to allow the pin 126 to project through it. In one form of the roof it comprises a transparent element 133 (see FIG. 25C) set into a hole 131.

The transparent element 133 can be a plate or it can be a magnifier in order to allow inspection of the lens.

The upper case 102 and the lower case 104 when connected provide a storage chamber 103 (see FIG. 25C). To start the storage process, a lens 106 and if used some saline or balanced salt are put in place in the lower case 104. The lens 106 has a central opening of a diameter that it will drop onto the pin 126 to a point where it will rest circumferentially on the platform 136 or shoulders 138 at sides of the platform 136 on opposite sides of the well 118.

The structure and process for closing the upper and lower cases 102 and 104 are similar to that described above with respect to the embodiment shown in FIGS. 1-17. Specifically, in the lower case 104 are a pair of circumferentially shaped slots 32 and 34 which provide openings 36 and 38 respectively (see FIG. 22B). Mating tabs 56 and 58 project from the lower side of the upper case 102 (as shown in FIGS. 10, 11 and 12). To do the connection then, the upper case 102 is placed so that the tabs 56 and 58 are ready to enter the slots 32 and 34, then they (the upper and lower cases) are rotated relatively to close them. At that point the detent 39 enters and snaps into the opening 72 (see FIG. 9) formed as part of the upper case 102, to maintain the closing position against inadvertent opening. To open the assembly, the upper and lower case are rotated oppositely to the closing rotation with sufficient force to release the detent 39.

Then the lens can be removed. As described above, one procedure is the use of a lens inserter (also called a lens gripper) that can be used to both remove the lens from the lens holder and insert it in the intended eye. In particular the lower fork arm and the upper fork arm each terminate in gripping portions that are operable to be spaced apart and to close together to grip the lens remove it from the lens holder, and then subsequently upon insertion to release the lens in the eye.

Figure 26:
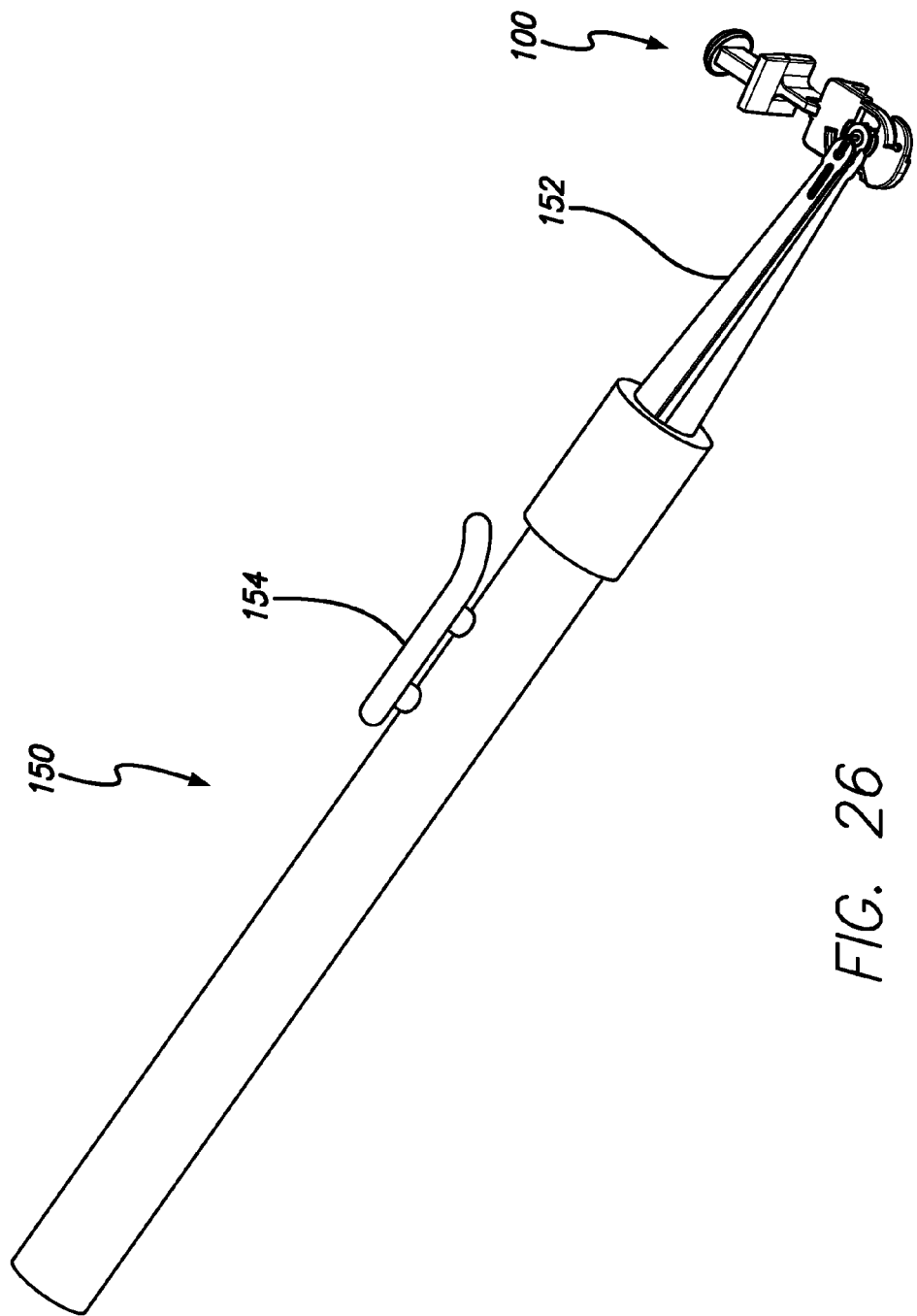
FIG. 26 is a view of an inserter in position with the lens holder apparatus.

Such a lens inserter 150 is shown in FIG. 26 in position at a lens holder 100. It has a gripping mechanism 152 operated by a lever 154.

Figure 27:
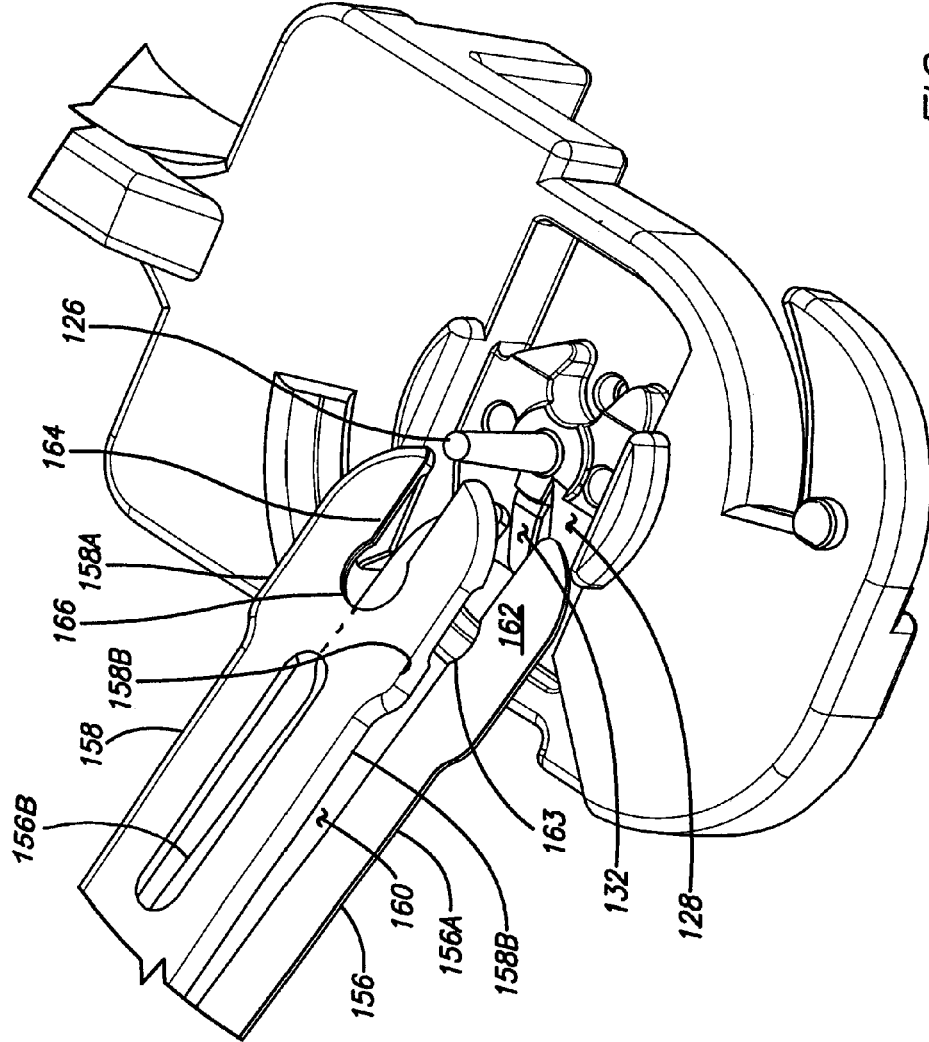
FIG. 27 is a perspective detailed view of an inserter being moved along the ramp of the lower case.
Figure 28:
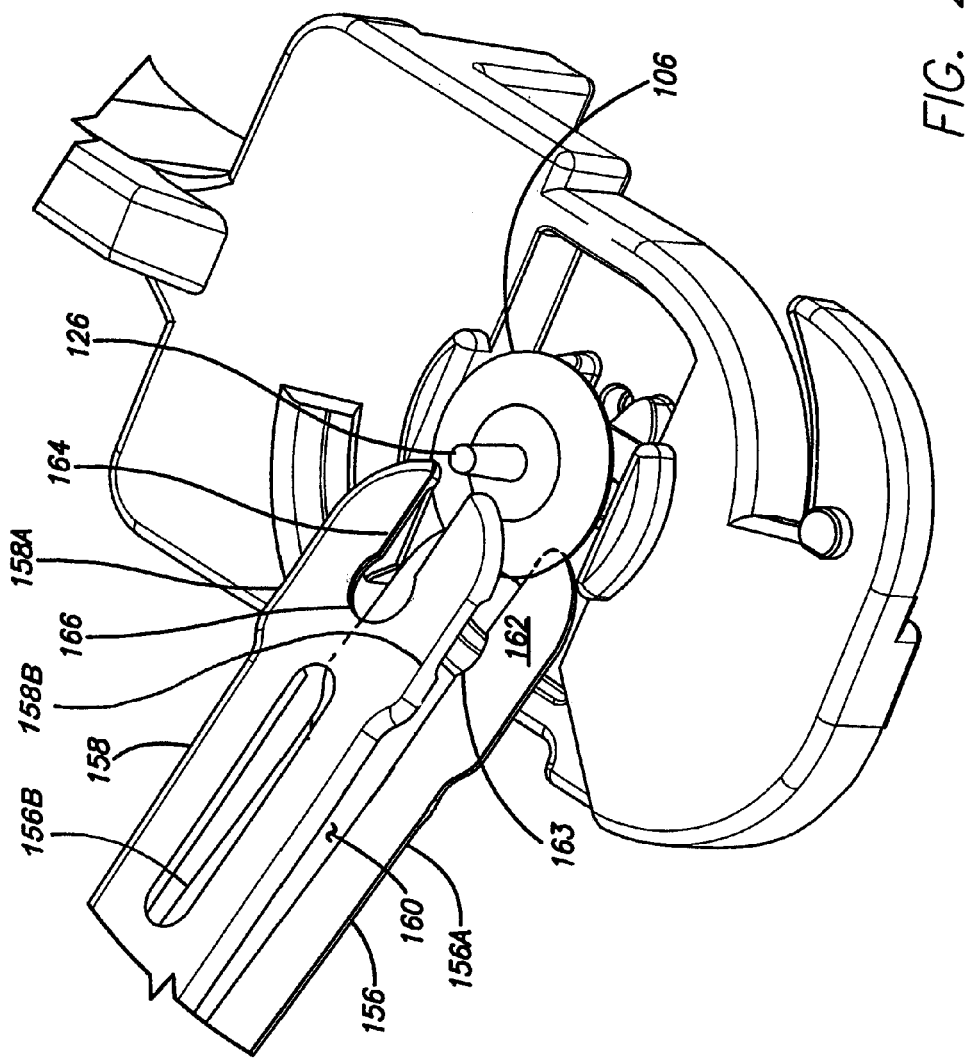
FIG. 28 is a perspective detailed view of an inserter being moved along the ramp of the lower case and a lens.

FIGS. 27 and 28 show how the inserter is used. In FIG. 27 there is no lens shown so as to make it easier to see the gripping mechanism moving on the ramp and FIG. 28 shows the gripping mechanism capturing a lens. The gripping mechanism 152 has a lower fork arm 156 and an upper fork arm 158. The lens inserter 150 operates through the lever 154 to allow the upper and lower fork arms 156 and 158 to have a separated position and then closes them to grip the lens.

The lower fork arm 156 has spaced apart forks 156A and 156B which are mirror configured to provide a slot 160 between them that extends openly to an end 162 of the lower fork arm 156. The forks 156A and 156B are spaced apart sufficiently to pass on each side of the pin 126. It also can have a curved portion 163 to facilitate locating it at the pin 126.

The upper fork arm 158 has spaced apart forks 158A and 158B defining a slot 164 which has a length such that when the pin 126 contacts its back end 166, the upper and lower fork arms will be in the best gripping position with the lens between them. Then the fork arms can be closed on each other to grip the lens and remove it from the pin. The gripping position has the function of lifting the lens off the pin as well as facilitating inserting the lens into an eye In use the lens inserter 150 is moved into a position such that the lower fork arm 156 is on the ramp 128 sufficiently away from the pin 126 as to not cause any unintended hitting of the lens 106. It is then moved toward the pin 126 along the ramp 128 wherein the slots of the upper and lower fork arms, pass the pin 126 until the pin 126 contacts the back end 166 of the slot 164 of the upper fork arm 158. By using the ramp to guide the upper and lower fork arms in their open position, they will be guided correctly to place the lens between them, and to not contact the lens until they are closed upon it.

At that point the lens will be correctly positioned between the upper fork arm and the lower fork arm which are then operated to close together, grip the lens and allow the lens to be lifted off the pin.

Then the inserter is used to insert the lens into the eye.

While the invention is described in terms of a specific embodiment, other embodiments could readily be adapted by one skilled in the art. Accordingly, the scope of the invention is limited only by the following claims.

The foregoing Detailed Description of exemplary embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations within the scope of the invention will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . . "

The invention claimed is:

1. A method for transporting and accessing a lens of the type used for eye implantation comprising;
    providing a lens holder with a lens comprising:
        a case having a storage chamber adapted to contain a lens in a substantially fixed position, the case comprising two connectable portions which before connection allow access to the storage chamber to place a lens therein and when connected close the storage chamber, the connectable portions comprising an upper case portion and a lower case portion which when connected define the storage chamber, the lower case portion having a lens positioning structure whereby a lens in the storage chamber is held in a substantially fixed position, the positioning structure comprising a pin extending upwardly from the lower case portion and the lower case portion having a lens access structure comprising a ramp extending from a lower position proximate an outer periphery of the lower case and upwardly toward the pin; and
        a lens on the pin; and
    providing a lens inserter having a lower fork arm and an upper fork arm, the upper and lower fork arms having an open position in which they are spaced apart and a closed position in which they are brought together and each of them having spaced apart forks defining a fork separation space in each of them;
    moving the lens inserter such that the lower fork arm contacts the ramp and is guided upwardly on the ramp toward the pin such that the lens becomes positioned between the lower and upper fork arms and the pin is in the fork separation spaces whereby the lens is centrally located between the upper and lower fork arms; and
    moving the upper and lower fork arms together to grip the lens; and
    lifting the lens off the pin in the grip of the lens inserter.

2. The method of claim 1 further comprising:
    providing a tab extending diametrically toward the pin and upwardly of the ramp, and substantially centrally of the ramp and the lens inserter being further guided by the tab being in the fork separation space between the forks of the lower fork arm.

3. The method of claim 1 further wherein the lens holder has a saline or balanced salt solution liquid in the storage chamber.

4. The method of claim 3 further wherein the lens holder has drain holes in the bottom of the lower case.

* * * * *